United States Patent
Kido et al.

(10) Patent No.: US 8,287,887 B2
(45) Date of Patent: Oct. 16, 2012

(54) ANTIGEN-AND-DRUG VEHICLE COMPRISING SYNTHETIC PEPTIDE, AND MUCOSAL VACCINE USING THE SAME

(75) Inventors: Hiroshi Kido, Tokushima (JP); Tsunetomo Takei, Tokushima (JP); Dai Mizuno, Tokushima (JP)

(73) Assignee: The University of Tokushima, Tokushima (JP)

( * ) Notice: Subject to any disclaimer, the term of this patent is extended or adjusted under 35 U.S.C. 154(b) by 0 days.

(21) Appl. No.: 12/936,075

(22) PCT Filed: Mar. 30, 2009

(86) PCT No.: PCT/JP2009/056508
§ 371 (c)(1),
(2), (4) Date: Dec. 17, 2010

(87) PCT Pub. No.: WO2009/123119
PCT Pub. Date: Oct. 8, 2009

(65) Prior Publication Data
US 2011/0110971 A1 May 12, 2011

(30) Foreign Application Priority Data
Apr. 2, 2008 (JP) ................................. 2008-096244

(51) Int. Cl.
*A61K 45/00* (2006.01)
*A61K 39/12* (2006.01)
(52) U.S. Cl. .................................. 424/278.1; 424/204.1
(58) Field of Classification Search ........................ None
See application file for complete search history.

(56) References Cited

FOREIGN PATENT DOCUMENTS
EP 1 930 025 6/2008
WO 2007/018152 2/2007

OTHER PUBLICATIONS

Macy, Seminars in Veterinary Medicine and Surgery, 12(3):206-211, 1997.*
Lycke et al, Essen. Mucosal. Immunol., 1996, pp. 563-580.*
Pokric (Periodicum Biologorum, 101(4):283-302, 1999).*
Allison, Int. J. Technol. Assess. Health Care, 1994 Winter 10(1):107-20.*
Gordon et al, J. Infectious Diseases, 171:1576-1585, 1995.*
Threadgill et al (Vaccine 16(1):76-82, 1998).*
Fritz et al (Vaccine, 22:3274-3284, 2004).*
International Search Report issued Jun. 9, 2009 in International (PCT) Application No. PCT/JP2008/056508.
Tsunemotoa Takei et al., "Hto Hai Surfactant Tanpakushitsu-C (SP-C) to sono Yudotai no Koto to Hyomen Kassei ni Tsuife", Journal of Japanese Medical Society for Biological Interface, vol. 29, pp. 65-68, (1998).

* cited by examiner

*Primary Examiner* — Patricia A Duffy
(74) *Attorney, Agent, or Firm* — Wenderoth, Lind & Ponack, L.L.P.

(57) ABSTRACT

The present invention is an antigen-and-drug (AD) vehicle and a mucosal vaccine utilizing a novel synthetic peptide. The antigen-and-drug (AD) vehicle is capable of inducing the production of secretory IgA antibodies, and is a complex of a synthetic peptide having the following amino acid sequence: PVHLKRLm (e.g., peptide of SEQ ID NO 1, 6, or 7) or KnLm (e.g., peptide of SEQ ID NO 2, 3, or 8), and a lipid(s). The mucosal vaccine is obtainable by allowing a mucosal-immunity-IgA-inducing amount of an antigen to coexist with, contact, be captured by, or be adsorbed onto the AD vehicle.

3 Claims, No Drawings

SEQUENCE LISTING

<160> NUMBER OF SEQ ID NOS: 9

<210> SEQ ID NO 1
<211> LENGTH: 17
<212> TYPE: PRT
<213> ORGANISM: Artificial Sequence
<220> FEATURE:
<223> OTHER INFORMATION: Synthetic construct

<400> SEQUENCE: 1

Pro Val His Leu Lys Arg Leu Leu Leu Leu Leu Leu Leu Leu Leu
1               5                   10                  15

Leu

<210> SEQ ID NO 2
<211> LENGTH: 22
<212> TYPE: PRT
<213> ORGANISM: Artificial Sequence
<220> FEATURE:
<223> OTHER INFORMATION: Synthetic construct

<400> SEQUENCE: 2

Lys Lys Lys Lys Lys Lys Leu Leu Leu Leu Leu Leu Leu Leu Leu
1               5                   10                  15

Leu Leu Leu Leu Leu Leu
            20

<210> SEQ ID NO 3
<211> LENGTH: 17
<212> TYPE: PRT
<213> ORGANISM: Artificial Sequence
<220> FEATURE:
<223> OTHER INFORMATION: Synthetic construct

<400> SEQUENCE: 3

Lys Lys Lys Lys Lys Lys Leu Leu Leu Leu Leu Leu Leu Leu Leu Leu

```
1               5                   10                  15
Leu

<210> SEQ ID NO 4
<211> LENGTH: 35
<212> TYPE: PRT
<213> ORGANISM: Homo sapiens
<220> FEATURE:
<221> NAME/KEY: MISC_FEATURE
<222> LOCATION: (1)..(35)
<220> FEATURE:
<221> NAME/KEY: MISC_FEATURE
<222> LOCATION: (1)..(35)
<223> OTHER INFORMATION: 1st to 35th amino acids of human SP-C

<400> SEQUENCE: 4

Phe Gly Ile Pro Cys Cys Pro Val His Leu Lys Arg Leu Leu Ile Val
1               5                   10                  15

Val Val Val Val Val Leu Ile Val Val Val Ile Val Gly Ala Leu Leu
            20                  25                  30

Met Gly Leu
        35

<210> SEQ ID NO 5
<211> LENGTH: 22
<212> TYPE: PRT
<213> ORGANISM: Artificial Sequence
<220> FEATURE:
<223> OTHER INFORMATION: Synthetic construct

<400> SEQUENCE: 5

Pro Val His Leu Lys Arg Leu Leu Leu Leu Leu Leu Leu Leu Leu Leu
1               5                   10                  15

Leu Leu Leu Leu Leu Leu
            20

<210> SEQ ID NO 6
<211> LENGTH: 21
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (18)..(21)
<223> OTHER INFORMATION: Xaa can be Leu or absent

<400> SEQUENCE: 6

Pro Val His Leu Lys Arg Leu Leu Leu Leu Leu Leu Leu Leu Leu Leu
1               5                   10                  15

Leu Xaa Xaa Xaa Xaa
            20

<210> SEQ ID NO 7
<211> LENGTH: 26
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (23)..(26)
<223> OTHER INFORMATION: Xaa can be Leu or absent

<400> SEQUENCE: 7

Pro Val His Leu Lys Arg Leu Leu Leu Leu Leu Leu Leu Leu Leu Leu
1               5                   10                  15
```

```
Leu Leu Leu Leu Leu Leu Xaa Xaa Xaa Xaa
            20                  25

<210> SEQ ID NO 8
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(8)
<223> OTHER INFORMATION: Xaa can be Lys or absent
<220> FEATURE:
<221> NAME/KEY: misc_feature
<222> LOCATION: (20)..(28)
<223> OTHER INFORMATION: Xaa can be Leu or absent

<400> SEQUENCE: 8

Lys Lys Lys Lys Xaa Xaa Xaa Xaa Leu Leu Leu Leu Leu Leu Leu Leu
1               5                   10                  15

Leu Leu Leu Xaa Xaa Xaa Xaa Xaa Xaa Xaa Xaa Xaa
            20                  25

<210> SEQ ID NO 9
<211> LENGTH: 6
<212> TYPE: PRT
<213> ORGANISM: Artificial Sequence
<220> FEATURE:
<223> OTHER INFORMATION: Synthetic construct

<400> SEQUENCE: 9

Pro Val His Leu Lys Arg
1               5
```

ANTIGEN-AND-DRUG VEHICLE COMPRISING SYNTHETIC PEPTIDE, AND MUCOSAL VACCINE USING THE SAME

This application is a U.S. National Stage of International application PCT/JP2009/056508, filed Mar. 30, 2009.

TECHNICAL FIELD

The present invention relates to an antigen-and-drug (AD) vehicle available for nasal, transmucosal, and transdermal administration, and also to a nasal/mucosal vaccine using the AD vehicle.

BACKGROUND ART

Patent Documents 1 and 2 describe in detail the disadvantages of conventional inactivated vaccines, toxoids, and the like, the present situations of development of mucosal vaccines and immunological adjuvants, etc.

As described in Patent Documents 1 and 2, it has been widely and deeply recognized that there is a need for a change from conventional vaccines for subcutaneous or intramuscular administration, for example, to mucosal vaccines that induce the production of IgA antibodies in mucosa, the route of natural infection with viruses. In particular, as next-generation vaccines for the 21st century, the development and commercialization of so-called mucosal vaccines that induce the production of IgA antibodies, local immunity, or mucosal immunity are wanted all over the world, but have not yet achieved.

To deal with these problems, the present inventors invented an antigen-and-drug (AD) vehicle that is a complex of pulmonary surfactant protein B and/or pulmonary surfactant protein C and a lipid(s), and also a mucosal vaccine comprising the AD vehicle and an antigen (Patent Document 1). The present inventors further found that the selective production of IgA antibodies and the production of both IgA and IgG antibodies are convertible by adjusting the weight ratio V/A between the AD vehicle amount (V) and the antigen amount (A), and have filed a patent application for a mucosal vaccine where such conversion is its mechanism of action (Patent Document 2). These Patent Documents 1 and 2 also disclose the effectiveness of fractions (peptides) of pulmonary surfactant proteins B and C.

Known examples of synthetic peptides associated with pulmonary surfactant proteins are those of Patent Documents 3 to 8.
[Patent Document 1] WO 2005/097182
[Patent Document 2] WO 2007/018152
[Patent Document 3] Japanese Patent No. 3009690
[Patent Document 4] JP-A-2004-305006
[Patent Document 5] JP-A-2006-504635
[Patent Document 6] WO 95/15980
[Patent Document 7] JP-A-2003-523348
[Patent Document 8] WO 02/32451

DISCLOSURE OF THE INVENTION

[Problems that the Invention is to Solve]
The present inventors examined various variants of pulmonary surfactant protein fractions for their antibody-production-enhancing effects. As a result, they found peptides that are smaller in size than the partial peptides disclosed in Patent Documents 1 and 2, but has a stronger antibody-production-inducing or -enhancing effect. In particular, they found such peptides are extremely effective in inducing the production of secretory IgA antibodies alone or the production of both secretory IgA antibodies and serum IgG antibodies.

The present invention aims to provide an antigen-and-drug (AD) vehicle and a mucosal vaccine utilizing such novel synthetic peptides.
[Means for Solving the Problems]
In order to solve the problems mentioned above, a first invention is an antigen-and-drug (AD) vehicle being a complex of a synthetic peptide and a lipid(s), the synthetic peptide having the following amino acid sequence:
PVHLKRLm wherein m is 11 to 15 (SEQ ID NO: 6) or 16 to 20 (SEQ ID NO: 7); or
KnLm wherein n is 4-8 and m is 11-20 (SEQ ID NO: 8).

In the antigen-and-drug (AD) vehicle, the synthetic peptide is preferably a peptide having the amino acid sequence set forth in SEQ ID NO: 1, 2, or 3.

The lipid in the AD vehicle is preferably at least one kind selected from the group consisting of phosphatidylcholine, dipalmitoylphosphatidylcholine, phosphatidylserine, phosphatidylglycerol, phosphatidylinositol, phosphatidylethanolamine, phosphatidic acid, lauryl acid, myristic acid, palmitic acid, stearic acid, and oleic acid, and more preferably a mixture of dipalmitoylphosphatidylcholine, phosphatidylglycerol, and palmitic acid.

A second invention is a mucosal vaccine obtainable by allowing a mucosal-immunity-IgA-inducing amount of an antigen to coexist with, contact, be captured by, or be adsorbed onto the above antigen-and-drug (AD) vehicle.

The antigen in the mucosal vaccine is preferably an inactivated antigen derived from an infectious pathogen or a detoxified toxin.

A third invention is an agent for prevention or treatment of allergy, obtainable by allowing a allergen, an allergen epitope, or an allergen-derived antigen to coexist with, contact, be captured by, or be adsorbed onto the above antigen-and-drug (AD) vehicle.

A fourth invention is a method for prevention or treatment of an infectious disease, which comprises administering the above mucosal vaccine at least twice.

A fifth invention is a method for prevention or treatment of allergy, which comprises administering the above agent for prevention or treatment of allergy at least twice.

In the methods of the fourth invention and the fifth invention, it is preferable to administer the vaccine at three times.
[Advantage of the Invention]
The advantages of the AD vehicle provided by the invention are characterized in that the production of secretory IgA antibodies alone and the production of both secretory IgA and serum IgG antibodies are effectively induced. The application and wide use of this AD vehicle will realize and spread the transmucosal/transdermal administration of mucosal vaccines against various infectious diseases, agents for prevention or treatment of allergy, and drugs. A nasal or a mucosal vaccine is an immunization method based on the actual conditions of natural infection, and thus has a much higher phylactic effect than conventional vaccines. Further, such nasal cavity mucosa IgA and IgG induced by the AD vehicle greatly improve medical care, health, and sanitation. This will also be long-awaited good news for persons engaged in the fields of medical care, health, and sanitation in the world. In addition, according to the invention, conventional and future biological preparations containing a vaccine, a toxoid, or the like, as well as a wide variety of other drugs, can be given functions and properties that enable transmucosal administration and transdermal administration thereof, which are easier than injection.

BEST MODE OF CARRYING OUT THE INVENTION

The AD vehicle (Antigen and Drug Vehicle) of the present invention is a complex of a lipid(s) and a synthetic peptide, which is designed to allow an antigen, a drug, or the like to be administered transmucosally or transdermally.

(1) Synthetic Peptide

This is a peptide having the amino acid sequence PVHLKRLm (m is 11 to 15 (SEQ ID NO: 6) or 16 to 20 (SEQ ID NO: 7) or KnLm (n is 4 to 8 and m is 11 to 20 (SEQ ID NO: 8). That is, PVHLKRLm has m consecutive L (Leu) residues added to the C-terminal side of PVHLKR (SEQ ID NO: 9). KnLm (SEQ ID NO: 8) has n K (Lys) residues on the N-terminal side and m L residues on the C-terminal side consecutively. PVHLKRLm wherein m is 16 is a known peptide of SEQ ID NO: 27 in Patent Document 2, and is excluded from the present invention.

Such a synthetic peptide is one of the following peptides, for example. In parentheses are shown codes for the peptides. An amino acid residue is represented by a one-letter code.

```
(SP-CL11):   PVHLKRLLLLLLLLLLL           SEQ ID NO: 1

(K6L16):     KKKKKKLLLLLLLLLLLLLLLL      SEQ ID NO: 2

(K6L11):     KKKKKKLLLLLLLLLLL           SEQ ID NO: 3
```

SEQ ID NO: 1 (SP-CL11) is the 7th-12th amino acid sequence (PVHLKR) of the amino acid sequence of pulmonary surfactant protein C (SP-C) plus eleven L (Leu) residues added thereto. SEQ ID NO: 2 (K6L16) has six K (Lys) residues on the N-terminal side and 16 L residues on the C-terminal side. SEQ ID NO: 3 (K6L11) has six K (Lys) residues on the N-terminal side and 11 L residues on the C-terminal side.

(2) Lipid

As a phospholipid(s), a phospholipid(s) contained in a pulmonary-surfactant are usable, preferable examples thereof including phosphatidylcholine, dipalmitoylphosphatidylcholine, phosphatidylserine, and phosphatidylglycerol. In addition, phosphatidylinositol, phosphatidylethanolamine, phosphatidic acid, sphingomyelin, and the like are also usable. Examples of usable fatty acids include lauryl acid, myristic acid, palmitic acid, stearic acid, palmitoleic acid, and oleic acid. Further, lipids derived from aquatic animals that exhibit active inflation of the lung, such as whales and dolphins, are also usable.

(3) Composition of AD Vehicle

The synthetic peptide is present in an amount of about 0.2 to about 12.0% by dry weight, and the lipid(s) is present in an amount of about 88 to about 99.8% by dry weight.

(4) Preparation of AD Vehicle

For example, 4 mg of synthetic peptide dissolved in methanol is mixed with 96 mg of lipid(s) dissolved in a chloroform-methanol mixture, then evaporated to dryness under reduced pressure using an evaporator, suspended in 10% ethanol, and freeze-dried. The dry product is then uniformly suspended in 5 mL of isotonic solution, such as a physiological saline solution or a phosphate buffer (PBS), for example. The obtained suspension is used as an AD vehicle solution (100 mg/5 mL). The vehicle is prepared fresh for each use. Ultrasonic waves, a homogenizer, a mixer, a shaker, and the like are usable for suspension.

The 96 mg of lipids may specifically be, for example, a mixture of 64.5 mg of phosphatidylcholine, 22.7 mg of phosphatidylglycerol, and 8.8 mg of palmitic acid.

(5) Preparation of Mucosal Vaccine

The AD vehicle solution is added to a vaccine stock solution in such a manner that the dry weight ratio V/A between the antigen amount (A) and the AD vehicle amount (V) in the resulting vaccine is as desired, followed by mixing to prepare a mucosal vaccine. For example, when the weight ratio V/A is 1, with respect to a vaccine stock solution having an antigen content of 50 mg/ml, the amount of the AD vehicle (50 mg/ml) solution prepared in (4) above to be added to 50 μL of such a vaccine stock solution is 50 μL. In order to make a uniform mixture, a homogenizer, a mixer, a shaker, a stirrer, and the like are usable.

"Antigen" herein includes bacteria-derived antigens, virus antigens, toxoids, and the like that are highly purified to a purity of about 90% or more for use in vaccines, allergens derived from cedar pollen or mites, and the like and having a purity of about 90% or more, proteins, glycoproteins, polysaccharides, nucleic acids, and the like. As the value A of the antigen mass, an actual measurement value may be used. Alternatively, a value calculated from the purity, specific activity, and molecular weight of the antigen, the antigen-antibody reaction, and the like may also be used.

The dry weight (A) of antigen in the mucosal vaccine of the invention is about 0.1 to about 50 μg/kg, and preferably about 0.3 to about 30 μg/kg. When the antigen is in such an amount, the V/A is preferably about 0.1 to 1.0 in order to preferentially and selectively induce the production of IgA antibodies. The V/A for inducing the production of both IgA and IgG antibodies may be within a range of about 1.0 to about 100, and preferably about 20 to about 50.

When the V/A is as above, about 60% or more of the antigen is bound to the AD vehicle, and the resulting mucosal immunity vaccine is capable of effectively inducing the IgA antibody production and/or IgG antibody production.

Further, in the method for prevention or treatment according to the invention, the vaccine is administered at least twice (first immunity and second immunity), and more preferably three times (first immunity, second immunity, and third immunity). By such multiple immunizations, the titers of IgA and IgG antibodies can be significantly increased. The two or three administrations are made at intervals of about 1 to 3 weeks, and preferably about 2 weeks.

Hereinafter, more specific details of the invention will be described with reference to examples; however, the invention is not limited to these examples.

EXAMPLE 1

Antibody-production-enhancing effects of mucosal vaccines were examined using mice.

(1) Preparation of Synthetic Peptide

The following peptides were chemically synthesized by a known method.

```
                                                (SEQ ID NO: 1)
SP-CL11:        PVHLKRLLLLLLLLLLL (SEQ ID NO: 2)
K6L16:          KKKKKKLLLLLLLLLLLLLLLL (SEQ ID NO: 3)
K6L11:          KKKKKKLLLLLLLLLLL (SEQ ID No: 4)
SP-C(1-35):     FGIPCCPVHLKRLLIVVVVVVLIVVVIVGALLMGL (SEQ ID No: 5)
RK-SP-CL:       PVHLRKLLLLLLLLLLLLLLLL
```

SP-C (1-35) (SEQ ID No: 4) is equivalent to the 1st-35th amino acid sequence of human pulmonary surfactant protein C, and is identical with SEQ ID NO: 21 of Patent Document 1. In RK-SP-CL (SEQ ID NO: 5), there are four more L residues on the C-terminal side than in SP-CL11 (SEQ ID NO: 1), and KR of the 5th-6th amino acid sequence of SP-CL11 is reversed to RK.

(2) Preparation of AD Vehicle

The synthetic peptides prepared in (1) above were each added to a mixture of three kinds of lipids (dipalmitoylphosphatidylcholine: DPPC, phosphatidylglycerol: PG, and palmitic acid: PA) to form a film-like phospholipid membrane, preparing AD vehicles: SSF-2 (containing SP-C (1-35)), SSF-3 (containing SP-CL11), SSF-4 (containing K6L16), SSF-5 (containing RK-SP-CL), and SSF-6 (containing K6L11). The composition of the mixture of three kinds of lipids is PA, PG, PA (75:25:10, w/w/w). Each peptide was added in an amount equivalent to 0.6 mol % of the lipid mixture.

A mucosal vaccine (SSF-1) formed only of the mixture of three kinds of lipids was also prepared.

(3) Production of Split Influenza Vaccine

Using a suspension prepared from embryonated eggs inoculated with influenza A virus strain Aichi/68/2/$H_3N_2$ ($1\times10^8$ PFU (plaque forming unit)) (supplied from Dr. Masanobu Ouchi, Institute of Microbiology, Kawasaki Medical University), a split influenza vaccine was prepared as follows. The virus suspension was dialyzed overnight with 0.004 M PBS (TAKARA BIO, Tokyo and Shiga, Japan), and then β-propiolactone (WAKO PURE CHEMICAL INDUSTRIES, Osaka, Japan) was added thereto in an amount of 0.05% of the fluid volume to a final concentration of 8 nM, followed by incubation in an ice bath for 18 hours. Subsequently, incubation was performed at 37° C. for 1.5 hours to hydrolyze β-propiolactone. Tween 20 (WAKO PURE CHEMICAL INDUSTRIES) was then added thereto to a final concentration of 0.1%. Diethylether (WAKO PURE CHEMICAL INDUSTRIES) in an amount equivalent to Tween was further added thereto, and then mixed by inversion at 4° C. for 2 hours. The thus-obtained mixture was centrifuged at 2,000 rpm for 5 minutes, thereby collecting the aqueous layer. Further, diethylether was removed from the aqueous layer using the Automatic Environmental SpeedVac System (SAVANT INSTRUMENTS, INC., New York, US), followed by filtration through a Millex 0.45-μm filter (MILLIPORE, Massachusetts, US) to give an inactivated split influenza vaccine (HA). An inactivated split influenza vaccine prepared using formalin in place of β-propiolactone is also usable.

(4) Preparation of Mucosal Vaccine

The AD vehicles (SSF-1 to SSF-6) prepared in (2) above were each mixed with the split influenza vaccine (HA) produced in (3) above, thereby preparing mucosal vaccines (HA+SSF-1 to HA+SSF-6). Specifically, each AD vehicle was suspended in PBS just before use to a concentration required for vaccine administration, and then subjected to supersonic treatment at room temperature for 5 minutes to give a uniform suspension. To the suspension was added the split influenza vaccine in an amount of 0.1 μg per 0.1 μg of the AD vehicle (dry weight). They were mixed in a vortex mixer, allowed to stand at room temperature for 1 hour, and then used.

(5) Animal

Six-week-old female BALB/c mice purchased from JAPAN SLC (Shizuoka, Japan) were used. All of the animal experiments were conducted in the animal house for infected animals (level P2) of the Laboratory Animal Center of the Medical Faculty of the University of Tokushima, and performed in accordance of the guidelines of the Animal Experiment Committee of the Medical Faculty of the University of Tokushima.

(6) Immunization

Nasal vaccination was performed as follows. Each of the mucosal vaccines of (4) above was diluted with a phosphate buffered saline (PBS) to give a 0.1 μg/μL PBS solution of the vaccine (dry weight), and then nasally administered in drops to the mice anesthetized with Ketalar (62.6 mg/kg) and Selactar (12.4 mg/kg) in such a manner that each vaccine solution was administered to both nasal cavities of a mouse in a dose of 1 μL per nostril, i.e., in a total dose of 2 μL. The same amount of PBS as that of the vaccine solution was administered to the control group. The virus antigen HA alone was also administered. Four weeks later, a second immunization was performed in the same manner as the first immunization. Further, a third immunization was performed with HA alone and HA+SSF-4 two weeks after the second immunization.

(7) Preparation of Mouse Nasal Cavity/Bronchoalveolar Lavage Fluids and Blood Serum Nasal cavity/bronchoalveolar lavage fluids and blood serum were prepared/collected from the mice two weeks after the second immunization, and virus-specific IgA and IgG were measured. With respect to HA alone and HA+SSF-4, IgA and IgG were measured similarly two weeks after the third immunization.

The abdomen and chest of the vaccine-treated mice were opened under pentobarbital anesthesia. After tracheotomy, an Atom intravenous catheter tapered to 3 Fr (ATOM MEDICAL, Tokyo, Japan) was inserted into the lung, and 1 ml of physiological saline solution was instilled thereinto and then collected. This operation was repeated three times, and 3 ml of the collected solution was employed as a bronchoalveolar lavage fluids. After the lung lavage fluids were collected, an Atom intravenous catheter was inserted from the opened trachea in the direction toward the nasal cavity, and 1 mL of physiological saline solution was instilled thereinto. Fluids draining from the nose were collected. The obtained fluids were employed as nasal lavage fluids. Further, blood was collected from the heart, and centrifuged at 5,000 rpm for 10 minutes to prepare a blood serum.

(8) Quantitative Determination of Anti-Influenza Antibody

The contents of anti-influenza IgA and IgG in the nasal cavity/bronchoalveolar lavage fluids and in the blood serum were determined by ELISA assay. The ELISA assay was performed according to the method of a Mouse ELISA Quantitation kit of BETHYL LABORATORIES (Texas, US). To each well of a 96-well Nunc-Immuno plate (Nalgen Nunc International, New York, US) was added 1 μg of vaccine and 100 μl of 1 μg/ml PBS solution of bovine serum albumin (BSA, SIGMA, Missouri, USA), and a reaction was performed at 4° C. overnight for immobilization. Subsequently, the wells were washed three times with a washing solution (50 mM Tris, 0.14 M NaCl, 0.05% Tween 20, pH 8.0) to remove the vaccine solution. To each well was added 200 μL of 50 mM Tris-HCl buffer (pH 8.0) containing 0.15 M NaCl and 1% BSA, followed by a blocking reaction at room temperature for 1 hour. Each well was washed three times with a washing solution. Then, 100 μL of the nasal lavage fluids, the lung lavage fluids, or the blood serum diluted to an appropriate volume with a sample-binding buffer (50 mM Tris, 0.15 M NaCl, 1% BSA, 0.05% Tween 20, pH 8.0) was added thereto, and allowed to react at room temperature for 2 hours. Using Goat anti-mouse IgA or IgG-horse radish peroxidase (HRP) (BETHYL LABORATORIES INC.) as a secondary antibody, a color reaction was performed using the TMB Microwell Peroxidase Substrate System (KIRKEGAARD & PERRY LABORATORIES, INC., Maryland, US). 100 µL of 2 M H$_2$SO$_4$ (WAKO PURE CHEMICAL INDUSTRIES) was added to each well to terminate the reaction, and the absorbance at 450 nm was measured using SPECTRAmax PLUS 384. As the standard for quantitative determination, the absorbance of 10 ng of anti-influenza IgA and IgG purified from the above-mentioned lung lavage fluids, which was determined in the same manner as above, was employed.

(9) Results

The results of the quantitative determination of anti-influenza antibodies are shown in Table 1. The amounts of anti-influenza IgA and/or IgG produced were greater in the groups that received the mucosal vaccines (HA+SSF-1 to HA+SSF-6) prepared by mixing the HA vaccine with SSF-1 to SSF-6, respectively, than in the group that received the HA vaccine alone. In particular, "SSF-3 containing SP-CL11", "SSF-4 containing K6L16", and "SSF-6 containing K6L11" were confirmed to have strong effects in enhancing the production of IgA and IgG antibodies, which are comparable to the effects of natural SP-C (1-35). Further, from the fact that the antibody-production-enhancing effects of SSF-1 and SSF-5 were nearly equal, it was confirmed that RK-SP-CL having an amino acid sequence partially modified from SSF-3 (SP-CL) is not much involved in the antibody production.

Further, after the third immunization with HA+SSF-4, the nasal mucus IgA antibody titer and the blood serum IgG antibody titer both greatly increased. These results confirm that in the treatment with the mucosal vaccine of the invention, the vaccine should be administered at least twice, and preferably three times.

TABLE 1

| Mucosal Vaccine | Anti-HA Specific Antibody in Nasal Cavity Lavage Fluids (IgA: ng/mL) | Anti-HA Specific Antibody in Blood serum (IgG: ng/mL) | AD Vehicle Constituents |
|---|---|---|---|
| Control | 28.4 ± 8.8 | 26.5 ± 8.4 | |
| HA | 27.7 ± 5.6 | 90.4 ± 56.6 | |
| HA (3) | 14.9 ± 12.8 | 281.6 ± 313.6 | |
| HA + SSF-1 | 69.5 ± 34.4 | 374.3 ± 176.8 | DPPC/PG/PA |
| HA + SSF-2 | 257.9 ± 90.7 | 1025.7 ± 281.8 | DPPC/PG/PA + SP-C (1-35) |
| HA + SSF-3 | 168.0 ± 71.4 | 435.0 ± 103.2 | DPPC/PG/PA + SP-CL11 |
| HA + SSF-4 | 167.5 ± 66.0 | 1473.7 ± 456.1 | DPPC/PG/PA + K6L16 |
| HA + SSF-4 (3) | 639.8 ± 204.4 | 2129.6 ± 626.7 | DPPC/PG/PA + K6L16 |
| HA + SSF-5 | 71.7 ± 11.3 | 276.9 ± 119.1 | DPPC/PG/PA + RK-SP-CL |
| HA + SSF-6 | 50.2 ± 56.9 | 1698.6 ± 540.9 | DPPC/PG/PA + K6L11 |

Note:
HA (3) and HA + SSF-4 (3) show the results after third immunization.

EXAMPLE 2

Antibody-production-enhancing effects of mucosal vaccines in a minipig model were examined.

(1) Summary of Method

Five- to ten-week-old Clawn minipigs (3 to 7 kg) (JAPAN FARM, Kagoshima) were used. Two weeks before the first immunization, nasal mucus samples were taken from the minipigs by the following method, and subjected to ELISA testing to confirm that the pigs were negative for anti-influenza antibodies. The minipigs were then used in the inoculation test. The antigen used herein is a formalin-inactivated, ether-split vaccine produced from influenza virus A strain New Caledonia (H1N1) (denoted as HA in the table, hereinafter referred to as "vaccine" in the description: from The Research Foundation for Microbial Diseases of Osaka University (Kagawa)). The amount of vaccine given to each minipig was 24 µg in terms of HA.

AD vehicles (SSF-2 containing SP-C (1-35), SSF-3 containing SP-CL11, and SSF-4 containing K6L16) were produced in the same manner as in Example 1. Each AD vehicle was mixed with the vaccine so that the ratio of the AD vehicle to the total protein weight of vaccine was 10:1, and 200 µL saline suspension was prepared according to the method described in a reference (Mizuno D, Ide-Kurihara M, Ichinomiya T, Kubo I, Kido H., Modified pulmonary surfactant is a potent adjuvant that stimulates the mucosal IgA production in response to the influenza virus antigen., J Immunol., 2006; 176:1122-30). The obtained suspensions were employed as mucosal vaccines (HA+SSF-2, HA+SSF-3, and HA+SSF-4), and administered to the minipigs sedated with a mixture of medetomidine (0.08 mg/kg) and midazolam (0.08 mg/kg) and then anesthetized with Ketalar (0.2 mg/kg) in such a manner that each mucosal vaccine was instilled using a rat oral sonde into both nasal cavities of a minipig in an amount of 100 µL per nostril. Nasal vaccination was thus performed.

A booster vaccination (second immunization) was performed three weeks after the first vaccination. From the first day of administration, nasal mucus samples and blood serum samples by blood collection from the jugular vein were taken every week for five weeks. In the vaccination weeks (week 0 and week 3), samples were taken two days before vaccination. Nasal mucus samples were taken as follows. Both nasal cavities of each minipig were wiped with a swab, the swab was then washed in 2 mL of saline, and nasal mucus fluids were was collected therefrom. Each sample was preserved at −80° C. prior to use in the test. A third immunization was performed with HA alone, HA+SSF-2, and HA+SSF-4 two weeks after the second immunization, and samples were taken two weeks after the third immunization (seven weeks after the first immunization).

The titers of anti-influenza IgA and IgG antibodies contained in each sample were measured by a method partially modified from ELISA of Example 1. Anti-influenza specific antibodies were detected as follows. The vaccine antigens used for nasal inoculation were each immobilized on the plate, and the antibody titers were measured using 4-fold dilutions of the minipig nasal fluid samples and also 10-fold dilutions of the minipig blood serum samples prepared by 2-fold serial dilution. With respect to 4-fold dilutions of the nasal fluid samples and 10-fold dilutions of the blood serum samples from the group that received a physiological saline solution (control group), the values [average absorbance at 450 nm+2×standard deviation] thereof were employed as cut-off reference values. A maximum dilution ratio that exhibits an absorbance greater than the reference value was taken as the titer of IgA or IgG antibodies in the sample. Samples having an absorbance not exceeding the reference value were considered to be below the detection limit (N.D.).

(2) Results

The results are as shown in Table 2. After the second immunization, the antibody titers in blood and nasal fluids both remarkably increased over one or two weeks. Comparing the final antibody titers in week 5 among groups, the titers of the anti-influenza antibodies, the nasal fluid IgA and the blood serum IgG, induced by the nasal inoculation of the vaccine antigen alone were 28 and 66, respectively, whereas in the groups that received AD-vehicle-containing mucosal vaccines, the IgA antibody titer was induced to 448 to 784, and the IgG antibody titer was induced to 832 to 1280. The three kinds of AD vehicles SP-C (1-35), K6L16, and SP-CL11 examined were all effective, and a statistically significant difference was not observed among the AD vehicles.

Further, with respect to the antibody titers after the third immunization with HA+SSF-2 and HA+SSF-4 (seven weeks after the first immunization), the nasal mucus IgA antibody titers further increased. In the case of HA+SSF-4, the blood serum IgG antibody titer also greatly increased. In the case where the measurement was continued until week 7 (week 7*) with only the second immunization, the titers of the nasal fluid IgA and the blood serum IgG greatly decreased. Accordingly, these results strongly show the effectiveness of the third immunization. These results also confirm that in the treatment using the mucosal vaccine of the invention, the vaccine should be administered at least twice, and preferably three times.

TABLE 2

|  | HA | HA + SSF-2 | HA + SSF-4 | HA + SSF-3 |
|---|---|---|---|---|
| Nasal fluid IgA Antibody titer (anti-A/New Caledonia) | | | | |
| Week 0 | N.D. | 96 ± 37 | 96 ± 37 | 224 ± 212 |
| Week 1 | 3 ± 2 | 88 ± 48 | 120 ± 99 | 232 ± 208 |
| Week 2 | 7 ± 7 | 104 ± 102 | 144 ± 81 | 184 ± 222 |
| Week 3 | 7 ± 7 | 144 ± 81 | 520 ± 405 | 354 ± 458 |
| Week 4 | 12 ± 5 | 384 ± 431 | 352 ± 460 | 336 ± 218 |
| Week 5 | 28 ± 27 | 448 ± 128 | 784 ± 869 | 768 ± 862 |
| Week 7 | 24 ± 23 | 832 ± 322 | 936 ± 342 | |
| Week 7* | 11 ± 9 | 152 ± 126 | 260 ± 216 | |
| Blood Serum IgG Antibody titer (anti-A/New Caledonia) | | | | |
| Week 0 | N.D. | N.D. | N.D. | N.D. |
| Week 1 | N.D. | N.D. | N.D. | N.D. |
| Week 2 | 2 ± 1 | 128 ± 91 | 33 ± 64 | 41 ± 60 |
| Week 3 | 1 ± 2 | 128 ± 91 | 67 ± 126 | 41 ± 60 |
| Week 4 | 132 ± 134 | 1280 ± 512 | 608 ± 483 | 801 ± 851 |
| Week 5 | 66 ± 67 | 1280 ± 512 | 896 ± 849 | 832 ± 820 |
| Week 7 | 28 ± 27 | 1266 ± 484 | 1250 ± 503 | |
| Week 7* | 26 ± 24 | 793 ± 481 | 555 ± 546 | |

Note:
Week 7* shows the results of measurement continued until week 7 with only the second immunization (without performing a third immunization).

The invention claimed is:

1. An antigen-and-drug (AD) vehicle, which is a complex of a synthetic peptide consisting of the amino acid sequence set forth in SEQ ID NO: 8, 2, or 3,
and a lipid mixture consisting of dipalmitoylphosphatidylcholine, phosphatidylglycerol, and palmitic acid.

2. A mucosal vaccine comprising inactivated viral influenza antigen and the antigen-and-drug (AD) vehicle of claim 1.

3. A method for prevention or treatment of an influenza infectious disease, which comprises administering the mucosal vaccine of claim 2 at least twice.

* * * * *